United States Patent [19]

Hope

[11] Plant 4,298

[45] Sep. 12, 1978

[54] KALANCHOE PLANT

[75] Inventor: Claude Hope, Carbago, Costa Rica

[73] Assignee: Mikkelsens, Inc., Ashtabula, Ohio

[21] Appl. No.: 823,853

[22] Filed: Aug. 11, 1977

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Beall & Jeffery

[57] ABSTRACT

A new asexually reproduced Kalanchoe characterized by its uniform floriferous flowering of light purple colored flowers and wide versatility in the sizes of flowering plants that can be produced having outstanding keeping qualities.

4 Drawing Figures

The present invention relates to a new and distinctive variety of kalanchoe plant, botanically known as Kalanchoe, developed by me through controlled breeding by crossing selected Swiss Rose clone #1 (seed parent) and a commercial seed strain of Swiss Rose (pollen parent). Both parents are unpatented. Asexual reproduction of stem cuttings has shown that the unique features of this new kalanchoe are stabilized and are reproduced true to type in successive propagations.

The following characteristics distinguish the new kalanchoe from both its parent varieties and other cultivated kalanchoes of this type known and used in the floriculture industry:

1. In comparison to the seed produced strain of Swiss Rose, the flower colors are quite similar but the quantity and placement of flowers of my new cultivar is greatly improved and the keeping qualities are superior. My new cultivar does not come true from seed.

2. In comparison to my seedling M-13, known by the cultivar name Adagio and a patent application for which is being filed simultaneously herewith, the plant growth and habits are quite similar, with the greatest differences being in a lighter flower color and narrower petals in the present cultivar. There is a tendency for the more mature flowers to fade in Largo. Flower petals of Largo are narrower and longer than in Adagio.

3. The light purple color of the flowers, the mature flowers fading slightly tending to give an overall dilution of color that remains pleasing rather than distracting.

4. Long keeping qualities of the flowers, which last in the home in full flower up to 10 to 12 weeks. Flowering is uniform. Mildew has not been observed to date on my new cultivar.

5. The large mound-type floral display, with the flower being twice the diameter of the extremities of the foliage.

6. Small compact foliage which allows pot to pot growing of the plants up to the time of flower development, a characteristic of great economic importance to the flowering pot plant producer.

7. The profuse self-branching habit which is of economic importance to the propagator and to the flowering pot plant producer. Furthermore, the self branching characteristic allows my new cultivar to be especially suited for small plant production.

8. The excellent and rapid rooting qualities of terminal stem cuttings, which root is 5 cm. pots in less than 21 days when the propagation media is 21°-22° C.

9. Intensive propagation research has shown that my new cultivar is ideally suited for production of miniature flowering kalanchoe plants as illustrated in FIG. 2 of the drawings. In the FIG. 2 plant, unrooted cuttings were stuck directly into 5 cm. pots and placed directly into short day treatment on 5.5 cm. centers. Such flowering plants can be used in terrariums or for combination flowering pots. Most kalanchoes become too tall or "stretched" when given this technique of producing miniature flowering plants.

10. Additional flowering trials indicate that my new cultivar also can be produced in 15 cm. pots by allowing additional time for plant development before pinching and giving short day treatment. Thus, my new cultivar has very broad versatility for pot plant production.

The accompanying colored photographs illustrate the overall appearance of this variety taken as face views of the plants and showing the colors as true as it is reasonably possible to obtain in colored reproductions of this type.

The illustrated large plant comprising FIG. 1 was grown under lights in a peat/perlite mixture in a 12 cm. clay pot, having been potted Dec. 20, 1976, pinched and placed into short day treatment Feb. 7, 1977, and flowered May 2, 1977. This plant was approximately 20 cm. in height and 25 cm. in diameter. The photograph was taken May 24, 1977. FIG. 2, as above noted, comprises plants the cuttings of which were placed in a 5 cm. pot, with the result being a miniaturization of the plants and reduced flower size.

The following is a detailed description of my new kalanchoe variety based on plants produced under commercial practices in Costa Rica and Ashtabula, Ohio. Color references are made to the Royal Horticultural Society Colour Chart except where general terms of ordinary dictionary significance are used.

Parentage: Selected clone #1 of Swiss Rose crossed with commercial seed strain of Swiss Rose, and specifically selected out of the fifth seedling generation.

Propagation:

(A) *type cutting.*—Vegetative terminal stem cuttings in 5 cm. pot.

(B) *Time to root.*—15-18 days at 22° C summer, 20-25 days at 21° C winter.

(C) *Rooting habit.*—Very rapid, profuse, dendritic, fibrous.

Plant description:

(A) *Form.*—Short, bushy, compact, vigorously upright.

(B) *Habit of growth.*—Slow, self-branching.

(C) *Foliage description.*—Small, yellow green, close internode, concave upward, nearly horizontal to slightly below horizontal. (1) Size: From 5 cm. wide to 6–7 cm. long, petiole 10 mm. base obtuse, apex round to obtuse. (2) Shape: Nearly round to slightly elliptical. (3) Texture: Glabrous, coriaceous. (4) Margin: Crenate to double crenate. (5) Color: Mature foliage, top side, yellow green, 146A, underside yellow green 148B, some purple to red marginal coloration.

Flowering description:

(A) *Flowering habits.*—Very floriferous, with the total inflorescence developing very uniformly on nearly every peduncle, thereby giving a massive mounded display of flowers, best described as a paniculate cyme. The subcymes usually carry 20 or more flowers.

(B) *Natural flowering season.*—Under good light conditions is late December, and under adverse light conditions is early to mid-January. Flowering time under controlled daylength at 22° C in smmer is 68–70 days; in winter is 85–87 days. Flowering time varies considerably with the intensity and duration of day light.

(C) *Flower buds.*—Typical for kalanchoes, being tubular with the petals wrapped; buds measure approximately 2 mm. in diameter by 10 mm. long before opening, to 15 mm. when open.

(D) *Flowers borne.*—Small flowering groups in cymes carried collectively on stiff wiry peduncles making up a paniculate cyme.

(E) *Quantity of flowers.*—Flowering shoots originate in nearly every leaf axil, with profuse flowering developing uniformly from apex to the crown.

(F) *Petals.*—(1) Shape: Long, elliptical. (2) Color: Top side when opening, red purple 73A, fading to red purple 73C; under side multi-shaded red purple 73B thru C. (3) Number of petals: Four measuring 3 mm. wide by 7–8 mm. long with total flower diameter of 16 mm.

(G) *Reproductive organs.*—(1) Stamens: Eight in number. (a) Anther: Anvil flate shape, color brown. (b) Filament: Translucent green in color. (c) Pollen color: Light creamy yellow. (2) Pistils: (a) Stigma: Coalesced irregular in shape, nearly colorless. (b) Style color: Light red. (c) Ovaries: Four in number, size 4 mm., color green before being pollinated; produces viable but variable seed.

Disease resistance: No diseases observed to date.

I claim:

1. A new and distinct cultivar of kalanchoe plant known by the cultivar name Largo and characterized particularly as to uniqueness by the combined characteristics of red purple flower color; excellent placement of flowers and superior keeping qualities; the large mound-type floral display; small compact foliage; profuse self-branching; excellent rooting qualities, and by the characteristic of being ideally suited for either normal or miniature flowering.

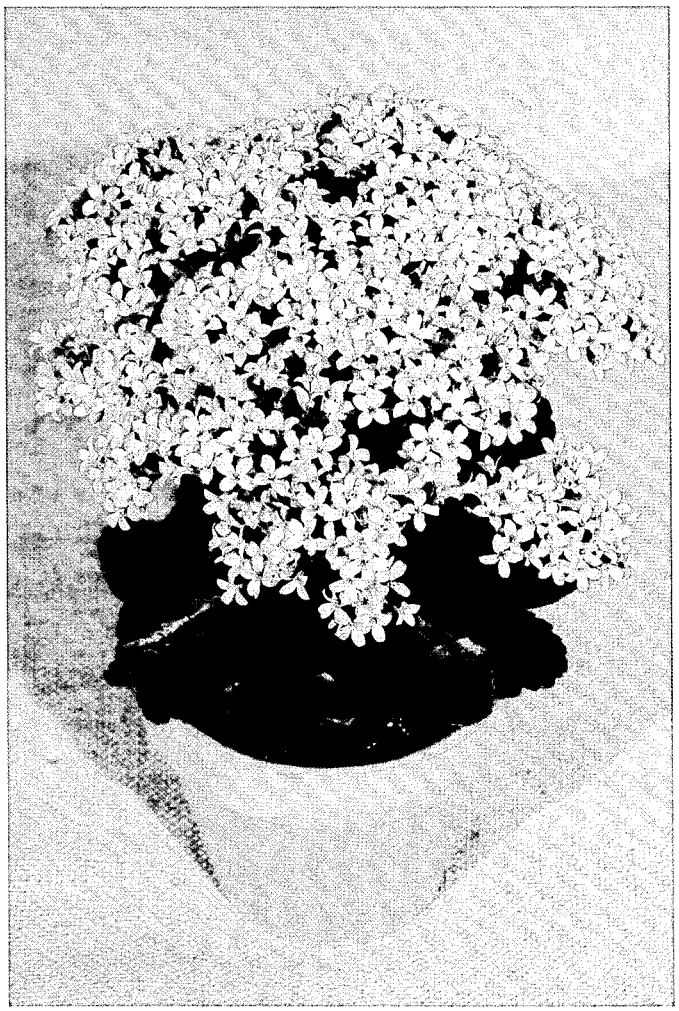

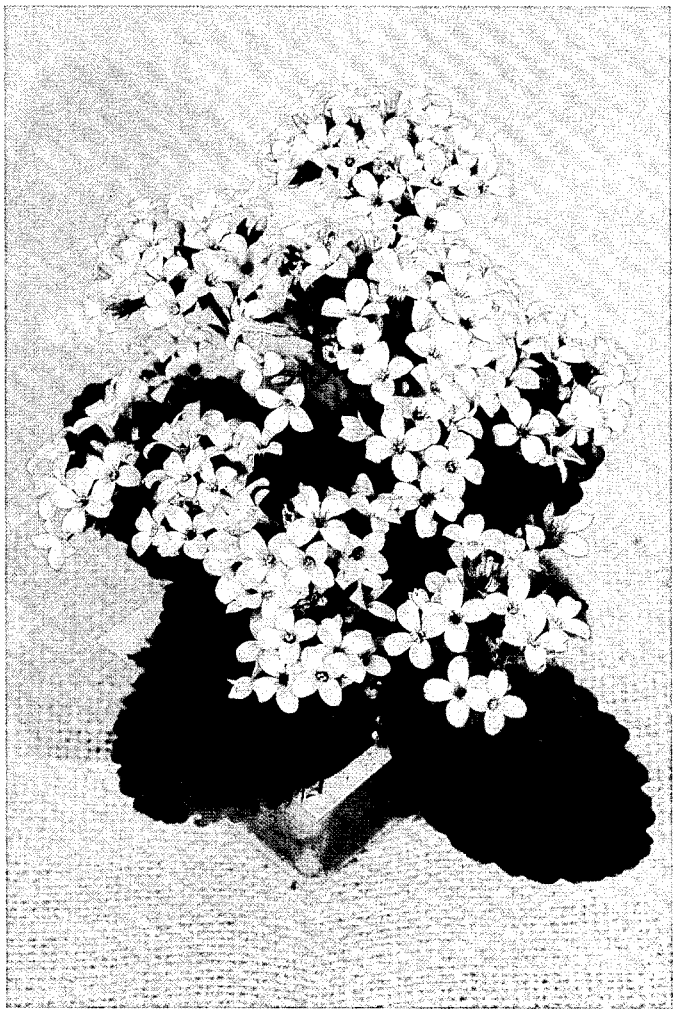

* * * * *